(12) United States Patent
Alani et al.

(10) Patent No.: US 7,432,294 B2
(45) Date of Patent: *Oct. 7, 2008

(54) PHARMACEUTICAL FORMULATIONS

(75) Inventors: Laman Alani, Morris Plains, NJ (US); Soumojeet Ghosh, Lansdale, PA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/546,673

(22) Filed: Oct. 12, 2006

(65) Prior Publication Data

US 2007/0032435 A1    Feb. 8, 2007

Related U.S. Application Data

(63) Continuation of application No. 09/576,097, filed on May 22, 2000, now Pat. No. 7,141,593.

(60) Provisional application No. 60/137,634, filed on Jun. 4, 1999, provisional application No. 60/177,020, filed on Jan. 19, 2000.

(51) Int. Cl.
    *A61K 31/425* (2006.01)
(52) U.S. Cl. ............... 514/365; 514/374; 424/456; 424/465; 424/502
(58) Field of Classification Search ............... 514/369, 514/365, 374; 424/456, 465, 502
    See application file for complete search history.

(56) References Cited

U.S. PATENT DOCUMENTS

| | | | |
|---|---|---|---|
| 5,086,165 A | 2/1992 | Marshall et al. | |
| 5,164,300 A | 11/1992 | Marshall et al. | |
| 5,171,662 A | 12/1992 | Sharma | |
| 5,183,826 A | 2/1993 | Bills et al. | |
| 5,250,563 A | 10/1993 | Chen et al. | |
| 5,256,677 A | 10/1993 | Sham et al. | |
| 5,264,223 A | 11/1993 | Yamamoto et al. | |
| 5,296,604 A | 3/1994 | Hanko et al. | |
| 5,342,625 A | 8/1994 | Hauer et al. | |
| 5,342,922 A | 8/1994 | Marshall et al. | |
| 5,354,866 A | 10/1994 | Kempf et al. | |
| 5,484,801 A | 1/1996 | Al-Razzak et al. | |
| 5,541,206 A | 7/1996 | Kempf et al. | |
| 5,756,123 A | 5/1998 | Yamamoto et al. | |
| 5,914,332 A | 6/1999 | Sham et al. | |
| 5,948,436 A | 9/1999 | Al-Razzak et al. | |
| 6,232,333 B1 | 5/2001 | Lipari et al. | |
| 7,141,593 B1 | 11/2006 | Alani et al. | |

FOREIGN PATENT DOCUMENTS

| | | |
|---|---|---|
| EP | 0 486 948 | 11/1991 |
| WO | 92/00750 | 1/1992 |
| WO | 94/14436 | 7/1994 |
| WO | 95/07696 | 3/1995 |
| WO | 95/09614 | 4/1995 |
| WO | 95/25504 | 9/1995 |
| WO | 97/01349 | 1/1997 |
| WO | 97/21685 | 6/1997 |
| WO | 98/22106 | 5/1998 |
| WO | 00/74677 | 12/2000 |

OTHER PUBLICATIONS

European Search Report for application 06114684.1, issued Nov. 17, 2006.*

* cited by examiner

*Primary Examiner*—David Lukton

(57) ABSTRACT

Improved pharmaceutical compositions are provided comprising one or more solubilized HIV protease inhibiting compounds having improved solubility properties in a medium and/or long chain fatty acid, or mixtures thereof, a pharmaceutically acceptable alcohol, and water.

25 Claims, 7 Drawing Sheets

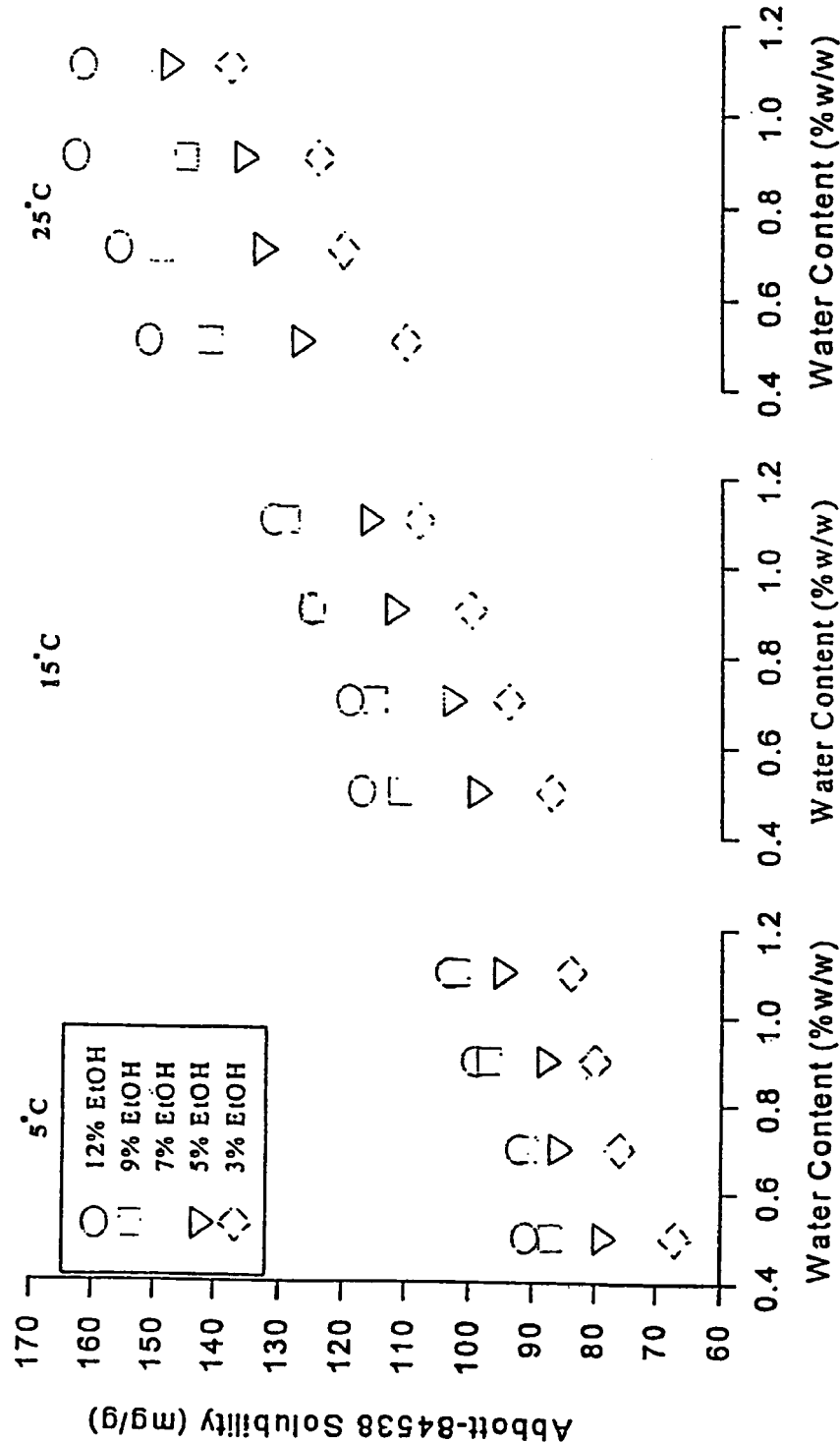
Figure 3. Solubility of Ritonavir Form II As a Function of Temperature, Water, Ethanol.

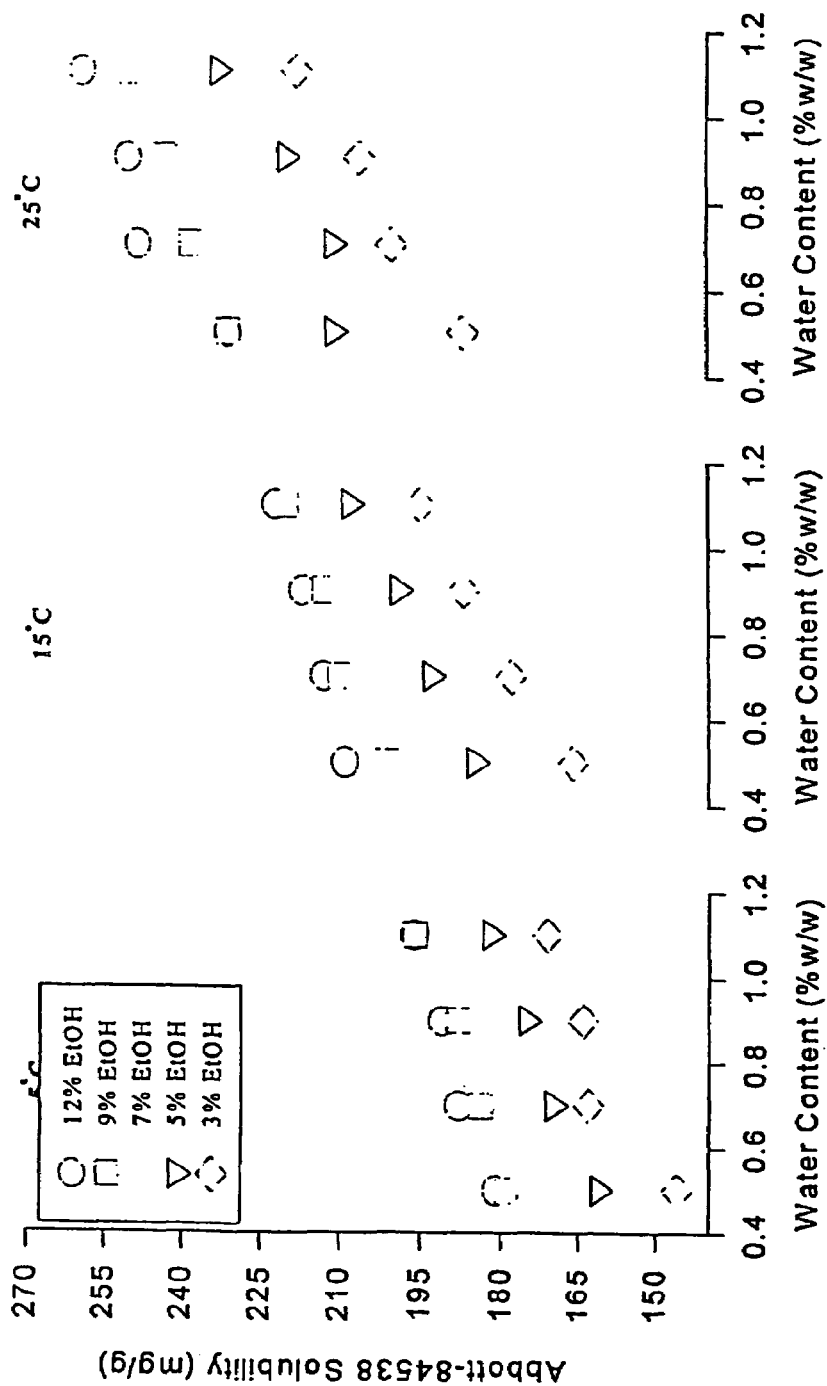
Figure 4. Solubility of Ritonavir Form I As a Function of Temperature, Water and Ethanol.

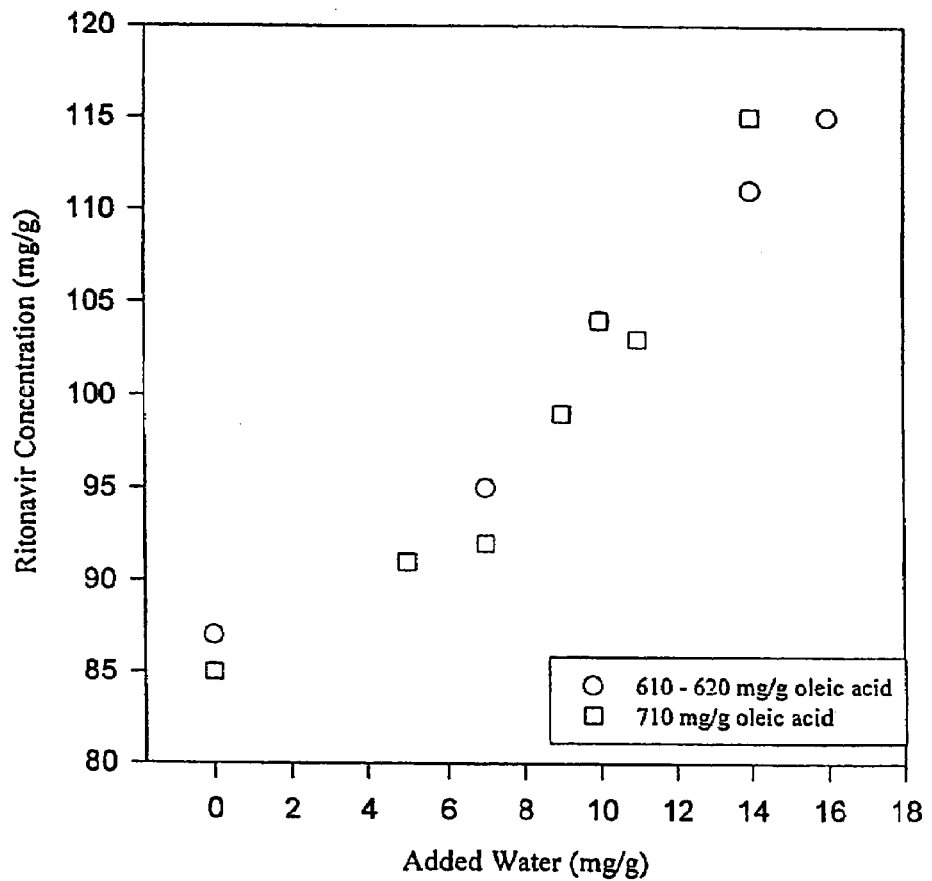
Figure 5. Effect of Added Water on Form II Solubility at 120 mg/g Ethanol.

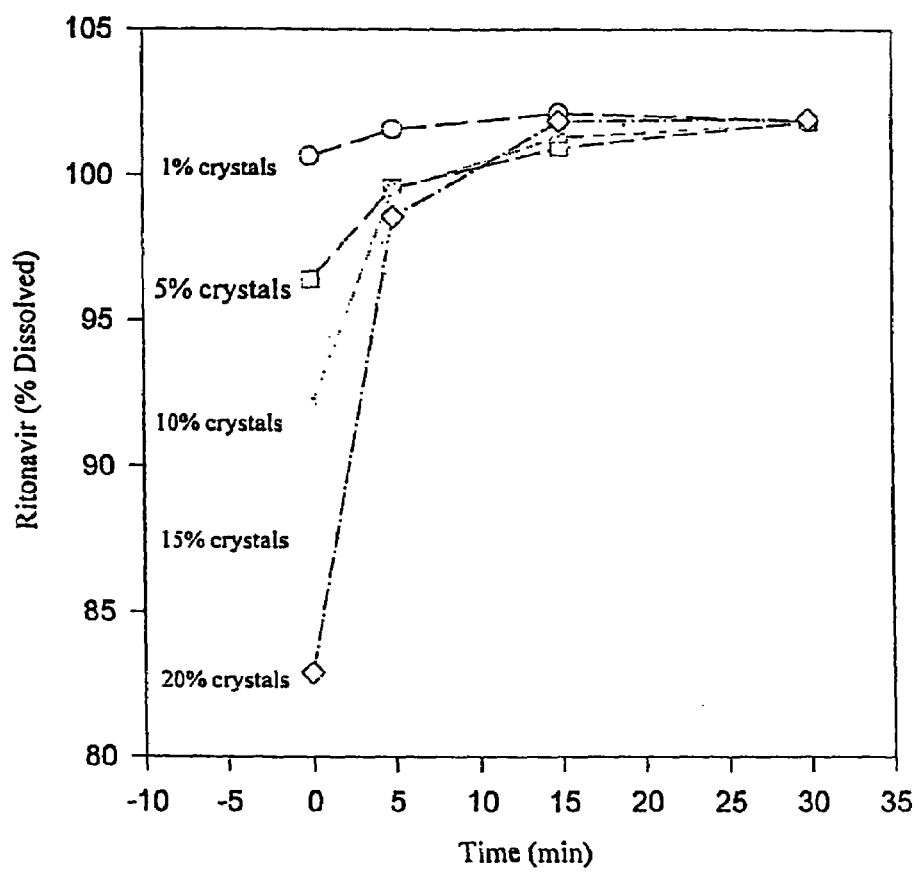
Figure 6. Dissolution Profiles of Ritonavir Form II Crystals in Modified Formulation Containing 30 mg/g Ethanol at 37°C.

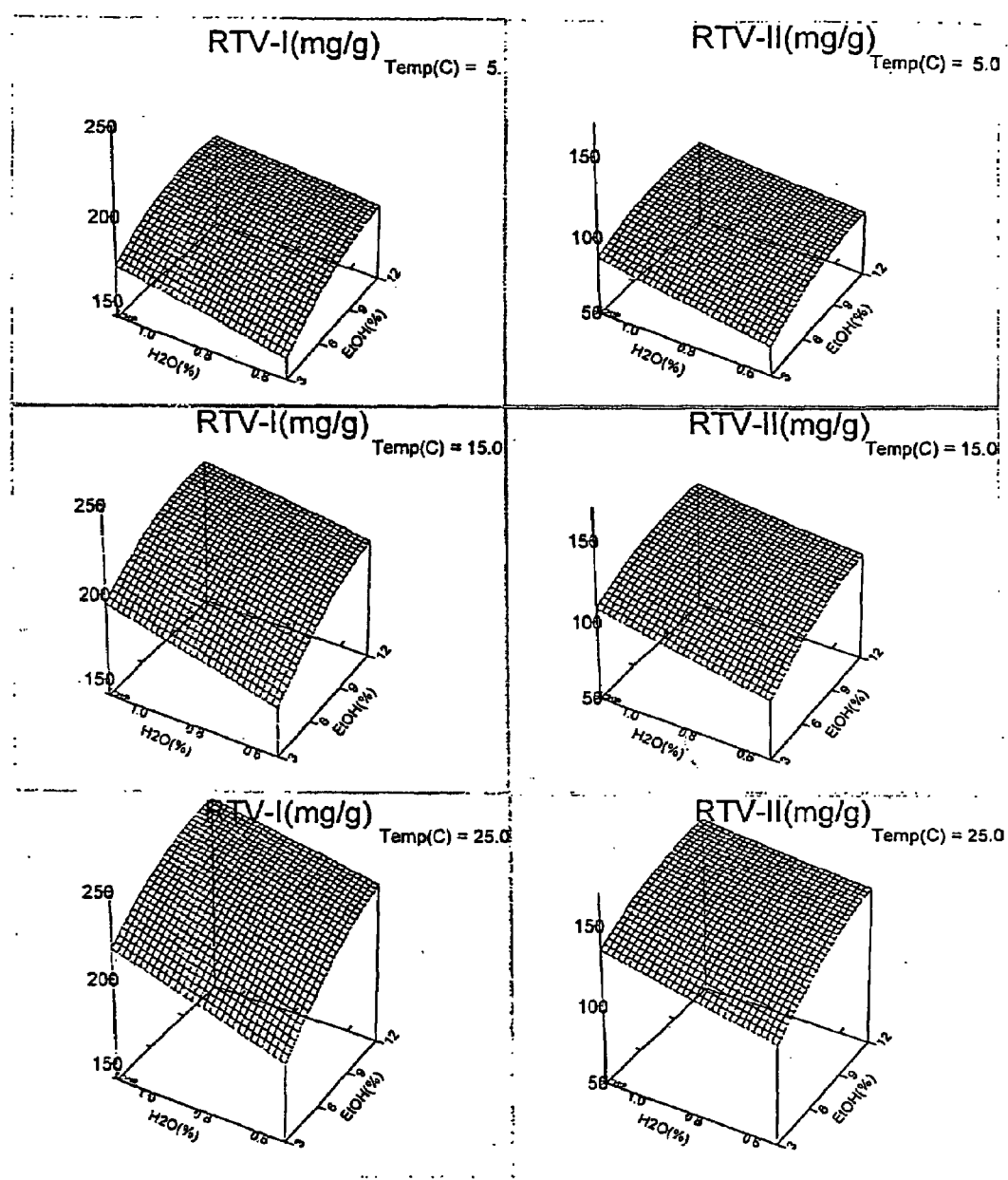
Figure 7. 3D Plots for the Solubility of Ritonavir Form I and II As a Function of Temperature, Water and Ethanol.

PHARMACEUTICAL FORMULATIONS

This application is a continuation of U.S. patent application Ser. No. 09/576,097, filed May 22, 2000, now U.S. Pat. No. 7,141,593, which claims the benefit of U.S. Provisional Application No. 60/137,634, filed Jun. 4, 1999, and U.S. Provisional Application No. 60/177,020, filed Jan. 19, 2000, all of which are incorporated herein by reference in their entireties.

TECHNICAL FIELD

This invention relates to improved pharmaceutical formulations comprising at least one HIV protease inhibiting compound in a pharmaceutically acceptable solution of a medium and/or long chain fatty acid, ethanol or propylene glycol, and water, wherein said HIV protease inhibiting compound contained therein has improved solubility properties.

BACKGROUND OF THE INVENTION

Inhibitors of human immunodeficiency virus (HIV) protease have been approved for use in the treatment of HIV infection for several years. A particularly effective HIV protease inhibitor is (2S,3S,5S)-5-(N-(N-((N-methyl-N-((2-isopropyl-4-thiazolyl)-methyl)amino)carbonyl)-L-valinyl) amino)-2-(N-((5-thiazolyl)-methoxy-carbonyl)-amino)-1,6-diphenyl-3-hydroxyhexane (ritonavir), which is marketed as NORVIR®. Ritonavir is known to have utility for the inhibition of HIV protease, the inhibition of HIV infection, and the enhancement of the pharmacokinetics of compounds which are metabolized by cytochrome $P_{450}$ monooxygenase. Ritonavir is particularly effective for the inhibition of HIV infection when used alone or in combination with one or more reverse transcriptase inhibitors and/or one or more other HIV protease inhibitors.

HIV protease inhibiting compounds typically are characterized by having poor oral bioavailability, and there is a continuing need for the development of improved oral dosage forms for HIV protease inhibitors having suitable oral bioavailability, stability, and side effects profiles.

Ritonavir and processes for its preparation are disclosed in U.S. Pat No. 5,541,206, issued Jul. 30, 1996, the disclosure of which is herein incorporated by reference. This patent discloses processes for preparing ritonavir which produce a crystalline polymorph of ritonavir, known as crystalline Form I.

Another process for the preparation of ritonavir is disclosed in U.S. Pat. No. 5,567,823, issued Oct. 22, 1996, the disclosure of which is herein incorporated by reference. The process disclosed in this patent also produces ritonavir as crystalline Form I.

Pharmaceutical compositions comprising ritonavir or a pharmaceutically acceptable salt thereof are disclosed in U.S. Pat. Nos. 5,541,206, issued Jul. 30, 1996; 5,484,801, issued Jan. 16, 1996; 5,725,878, issued Mar. 10, 1998; and 5,559,158, issued Sep. 24, 1996 and in International Application No. WO98/22106, published May 28, 1998 (corresponding to U.S. Ser. No. 08/966,495, filed Nov. 7, 1997), the disclosures of all of which are herein incorporated by reference.

The use of ritonavir to inhibit an HIV infection is disclosed in U.S. Pat. No. 5,541,206, issued Jul. 30, 1996. The use of ritonavir in combination with one or more reverse transcriptase inhibitors to inhibit an HIV infection is disclosed in U.S. Pat. No. 5,635,523, issued Jun. 3, 1997. The use of ritonavir in combination with one or more HIV protease inhibitors to inhibit an HIV infection is disclosed in U.S. Pat. No. 5,674,882, issued Oct. 7, 1997. The use of ritonavir to enhance the pharmacokinetics of compounds metabolized by cytochrome P450 monooxygenase is disclosed in WO 97/01349, published Jan. 16, 1997 (corresponding to U.S. Ser. No. 08/687,774, filed Jun. 26, 1996). The disclosures of all of these patents and patent applications are herein incorporated by reference.

Examples of HIV protease inhibiting compounds include:

N-(2(R)-hydroxy-1(S)-indanyl)-2(R)-phenylmethyl-4(S)-hydroxy-5 -(1-(4-(3-pyridylmethyl)-2(S)-N'-(t-butylcarboxamido)-piperazi nyl))-pentaneamide (for example, indinavir) and related compounds, disclosed in European Patent Application No. EP 541168, published May 12, 1993, and U.S. Pat. No. 5,413,999, issued May 9, 1995, both of which are herein incorporated by reference;

N-tert-butyl-decahydro-2-[2(R)-hydroxy-4-phenyl-3(S)-[[N-(2-qu inolylcarbonyl)-L-asparaginyl]amino]butyl]-(4aS,8aS)-isoquinoline-3(S)-carboxamide (for example, saquinavir) and related compounds, disclosed in U.S. Pat. No. 5,196,438, issued Mar. 23, 1993, which is incorporated herein by reference;

5(S)-Boc-amino-4(S)-hydroxy-6-phenyl-2(R)-phenylmethylhexanoyl -(L)-Val-(L)-Phe-morpholin-4-ylamide and related compounds, disclosed in European Patent Application No. EP532466, published Mar. 17, 1993, which is incorporated herein by reference;

1-Naphthoxyacetyl-beta-methylthio-Ala-(2S,3S) -3-amino-2-hydroxy-4-butanoyl 1,3-thiazolidine-4-t-butylamide (for example, 1-Naphthoxyacetyl-Mta-(2S,3S)-AHPBA-Thz-NH-tBu), 5-isoquinolinoxyacetyl-beta-methylthio-Ala-(2S,3S)-3-amino-2-h ydroxy-4-butanoyl-1,3-thiazolidine-4-t-butylamide, and related compounds, disclosed in European Patent Application No. EP490667, published Jun. 17, 1992 and Chem. Pharm. Bull. 40 (8) 2251 (1992), which are both incorporated herein by reference;

[1 S-[1 R-(R-),2S*])-$N^1$[3-[[[(1,1-dimethylethyl)amino]carbonyl](2-methylpropyl)amino]-2-hydroxy-1-(phenylmethyl)propyl]-2-[(2-quinolinylcarbonyl)amino]-butanediamide (for example, SC-52151) and related compounds, disclosed in PCT Patent Application No. WO92/08701, published May 29, 1992 and PCT Patent Application No. WO93/23368, published Nov. 25, 1993, both of which are herein incorporated by reference;

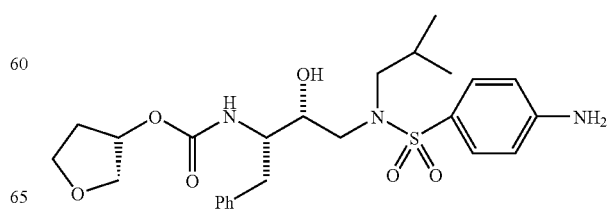

(for example, VX-478) and related compounds, disclosed in PCT Patent Application No. WO 94/05639, published Mar. 17, 1994, which is incorporated herein by reference;

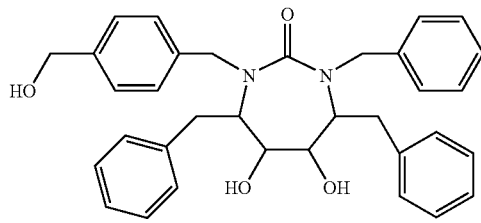

(for example, DMP-323) or

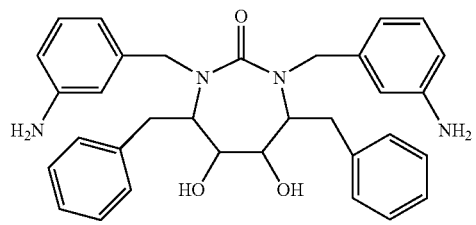

(for example, DMP-450) and related compounds, disclosed in PCT Patent Application No. WO 93/07128, published Apr. 15, 1993, which is incorporated herein by reference;

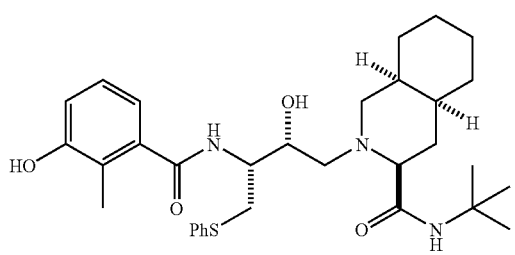

(for example, AG1343, (nelfinavir)), disclosed in PCT Patent Application No. WO 95/09843, published Apr. 13, 1995 and U.S. Pat. No. 5,484,926, issued Jan. 16, 1996, which are both incorporated herein by reference;

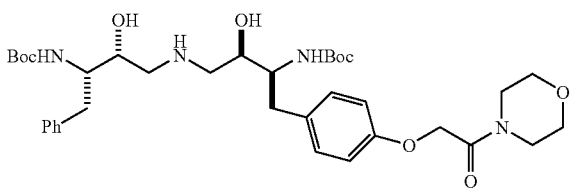

(for example, BMS 186,318) disclosed in European Patent Application No. EP580402, published Jan. 26, 1994, which is incorporated herein by reference;

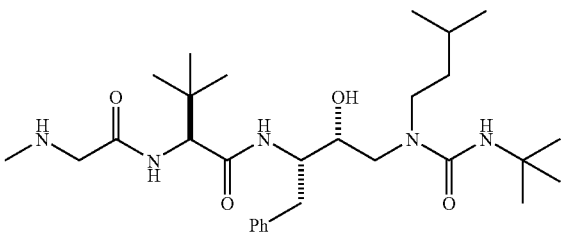

(for example, SC-55389a) and related compounds disclosed in PCT Patent Application No. WO 9506061, published Mar. 2, 1995, which is incorporated herein by reference and at 2nd National Conference on Human Retroviruses and Related Infections, (Washington, D.C., Jan. 29-Feb. 2, 1995), Session 88;

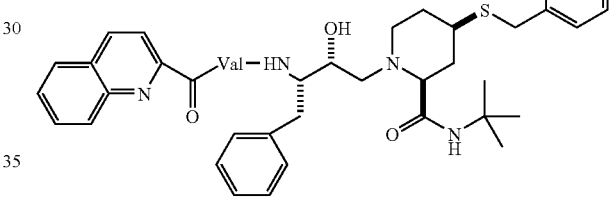

(for example, BILA 1096 BS) and related compounds disclosed in European Patent Application No. EP560268, published Sep. 15, 1993, which is incorporated herein by reference; and

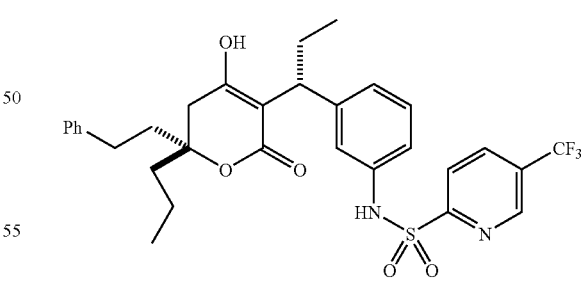

(for example, U-140690 (tipranavir)) and related compounds disclosed in PCT Patent Application No. WO 9530670, published Nov. 16, 1995, and U.S. Pat. No. 5,852,195, issued Dec. 22, 1998, the disclosures of both of which are herein incorporated by reference; or a pharmaceutically acceptable salt of any of the above.

Another example of an HIV protease inhibiting compound includes a compound of formula I:

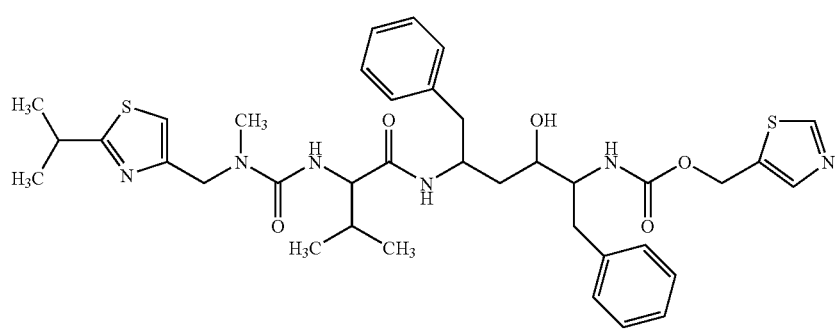

I or a pharmaceutically acceptable salt thereof, disclosed in PCT Patent Application No. WO 94/14436, published Jul. 7, 1994, and U.S. Pat. No. 5,541,206, issued Jul. 30, 1996, the disclosures of both of which are herein incorporated by reference.

The compounds of formula I are useful to inhibit HIV infections and, thus, are useful for the treatment of AIDS.

Another example of an HIV protease inhibiting compound is a compound of formula II:

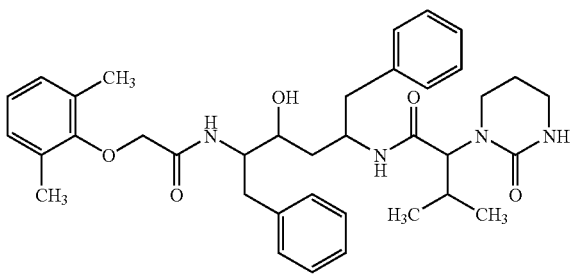

II and related compounds, or a pharmaceutically-acceptable salt thereof, as disclosed in U.S. patent application Ser. No. 08/572,226, filed Dec. 13, 1996 and U.S. patent application Ser. No. 08/753,201, filed Nov. 21, 1996, and International Patent Application No. WO 97/21685, published Jun. 19, 1997, the disclosures of which are herein incorporated by reference. A preferred compound of formula II is known as ABT-378 and has a chemical name of (2S,3S,5S)-2-(2,6-dimethylphenoxyacetyl)-amino-3-hydroxy-5-(2S-(1-tetrahydropyrimid-2-onyl)-3-methyl-butanoyl)amino-1,6-diphenylhexane, or a pharmaceutically-acceptable salt thereof. The preparation of this compound is disclosed in U.S. Pat. No. 5,914,332, issued Jun. 22, 1999, the disclosure of which is herein incorporated by reference.

Solubility is an important factor in the formulation of HIV protease inhibiting compounds. Compounds of formula I typically have an aqueous solubility of approximately 6 micrograms per milliliter at pH>2. This is considered to be extremely poor aqueous solubility and, therefore, a compound of formula I in the free base form would be expected to provide very low oral bioavailability. In fact, the free base form of a compound of formula I, administered as an unformulated solid in a capsule dosage form, is characterized by a bioavailability of less than 2% following a 5 mg/kg oral dose in dogs.

Acid addition salts of a compound of formula I (for example, bishydrochloride, bis-tosylate, bis-methane sulfonate and the like) have aqueous solubilities of <0.1 milligrams/milliliter. This is only a slight improvement over the solubility of the free base. This low aqueous solubility would not make practical the administration of therapeutic amounts of an acid addition salt of a compound of formula I as an aqueous solution. Furthermore, in view of this low aqueous solubility, it is not surprising that the bis-tosylate of a compound of formula I, administered as an unformulated solid in a capsule dosage form, is characterized by a bioavailability of less than 2% following a 5 mg/kg oral dose in dogs.

In order to have a suitable oral dosage form of a compound of formula I, the oral bioavailability of a compound of formula I should be at least 20%. Preferably, the oral bioavailability of a compound of formula I from the dosage form should be greater than about 40% and, more preferably, greater than about 50%.

One measure of the potential usefulness of an oral dosage form of a pharmaceutical agent is the bioavailability observed after oral administration of the dosage form. Various factors can affect the bioavailability of a drug when administered orally. These factors include aqueous solubility, drug absorption, dosage strength and first pass effect. Aqueous solubility is one of the most important of these factors. When a drug has poor aqueous solubility, attempts are often made to identify salts or other derivatives of the drug which have improved aqueous solubility. When a salt or other derivative of the drug is identified which has good aqueous solubility, it is generally accepted that an aqueous solution formulation of this salt or derivative will provide the optimum oral bioavailability. The bioavailability of the oral solution formulation of a drug is then generally used as the standard bioavailability against which other oral dosage forms can be measured.

For a variety of reasons, such as patient compliance and taste masking, a solid dosage form, such as capsules, is usually preferred over a liquid dosage form. However, oral solid dosage forms, such as a tablet or a powder, and the like, of a drug generally provide a lower bioavailability than oral solutions of the drug. One goal of the development of a suitable capsule dosage form is to obtain a bioavailability of the drug that is as close as possible to the bioavailability demonstrated by the oral solution formulation of the drug.

While some drugs would be expected to have good solubility in organic solvents, it would not necessarily follow that oral administration of such a solution would give good bioavailability for the drug. It has been found that a compound of formula I has good solubility in pharmaceutically acceptable organic solvents and that the solubility in such solvents is enhanced in the presence of a pharmaceutically acceptable long chain fatty acid. Administration of the solution as an encapsulated dosage form (soft elastic capsules or hard gelatin capsules) provides an oral bioavailability of as high as about 60% or more.

Thus, it would be an important contribution to the art to provide an improved pharmaceutical formulation comprising at least one solubilized HIV protease inhibiting compound having enhanced solubility properties.

BRIEF DESCRIPTION OF THE DRAWINGS

FIG. 3 illustrates the equilibrium solubility of Ritonavir Form II in the premix provided in Example 9.

FIG. 4 illustrates the equilibrium solubility of Ritonavir Form I in the premix provided in Example 9.

FIG. 5 illustrates the effect of added water on the solubility of Ritonavir Form II in oleic acid+ethanol co-solvent system.

FIG. 6 illustrates the dissolution profile of Ritonavir Form II crystals in the premix provided in Example 9.

FIG. 7 illustrates the 3D plots for the solubility of Ritonavir Form I and II as a function of temperature, water, and ethanol in the premix provided in Example 9.

SUMMARY OF THE INVENTION

Figure 1:
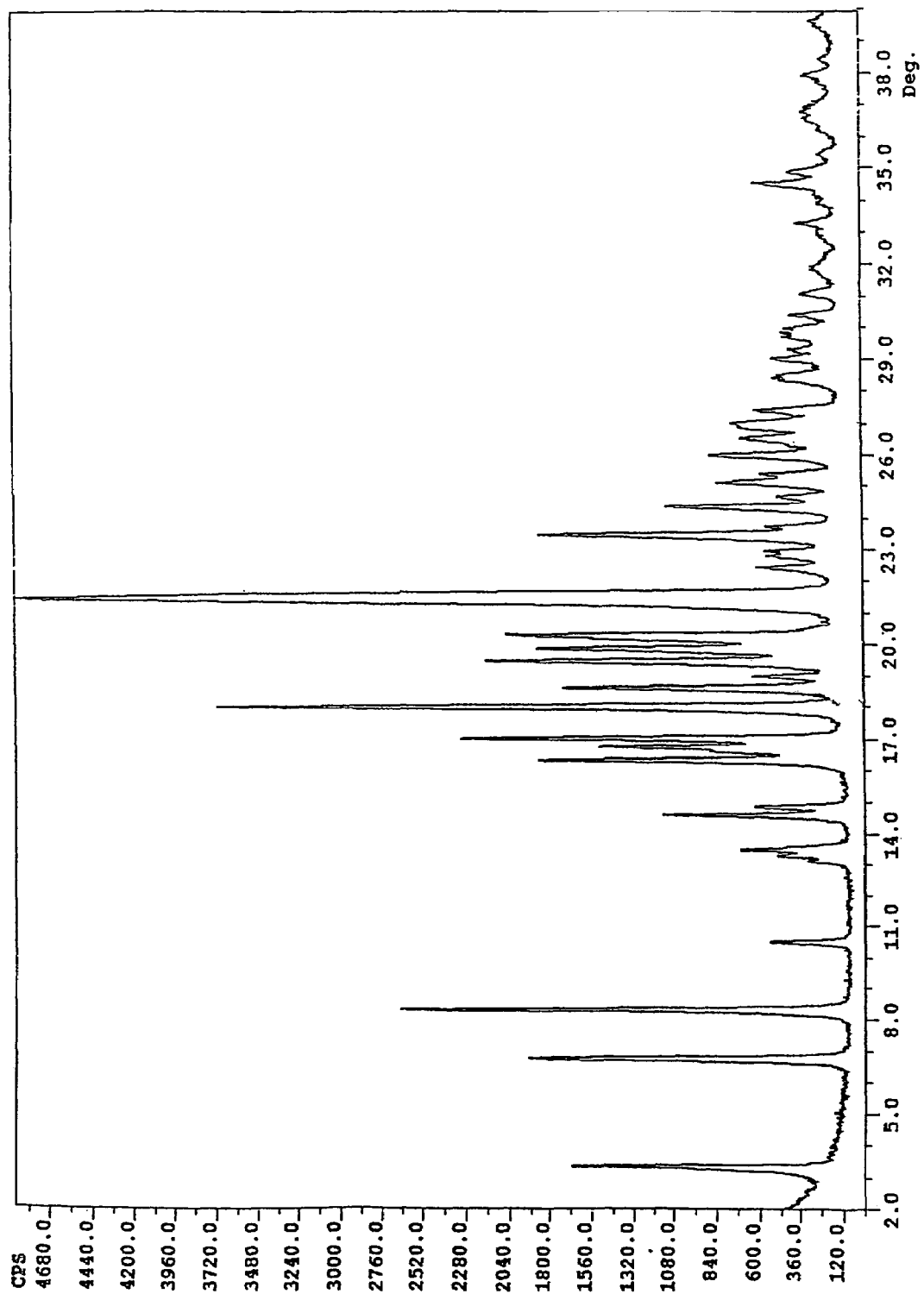
FIG. 1 illustrates the powder X-ray diffraction pattern of the substantially pure Form I crystalline polymorph of ritonavir.
Figure 2:
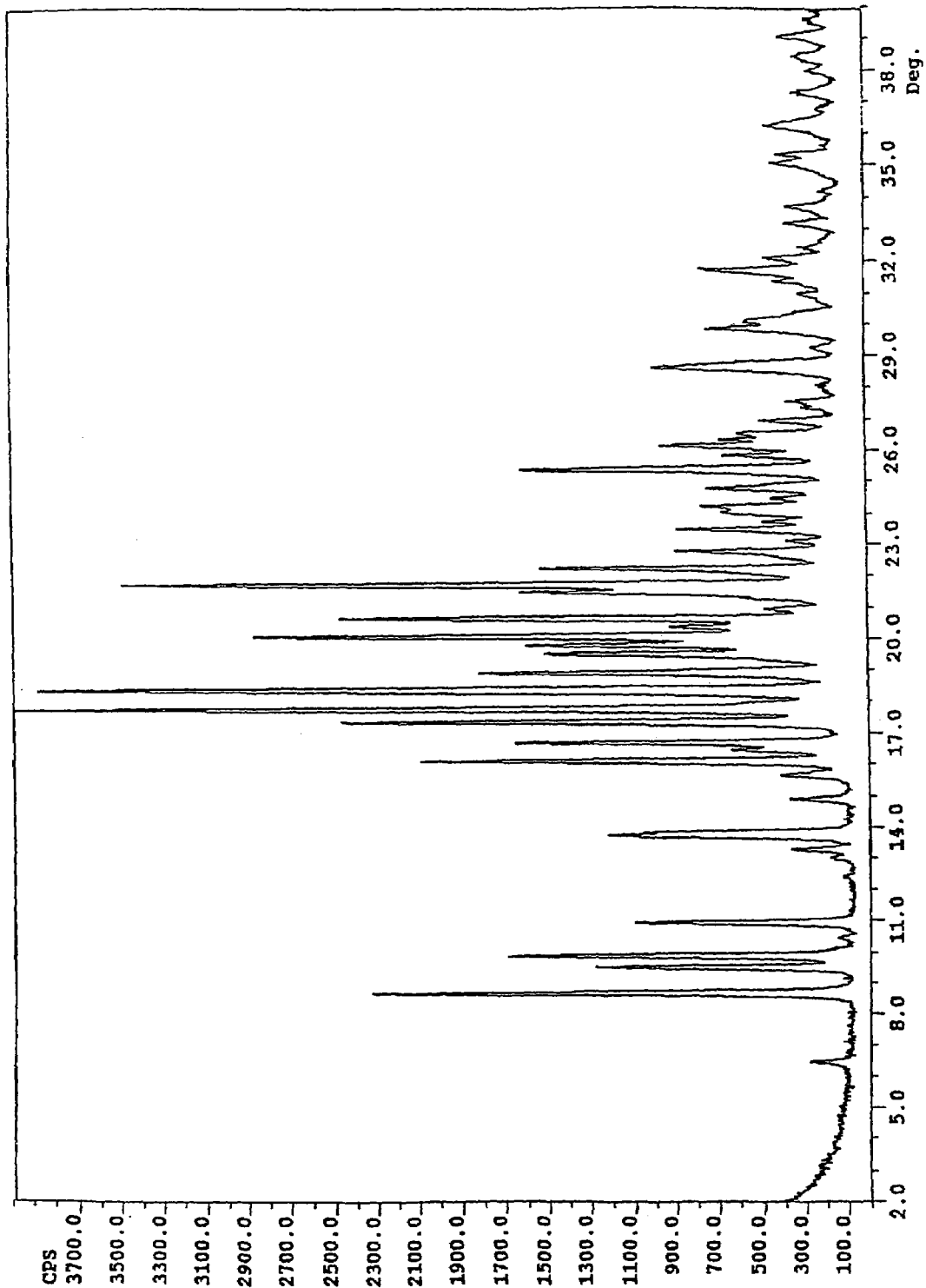
FIG. 2 illustrates the powder X-ray diffraction pattern of the substantially pure Form II crystalline polymorph of ritonavir.

The instant invention provides pharmaceutical compositions comprising at least one solubilized HIV protease inhibiting compound in a pharmaceutically acceptable solution of medium and/or long chain fatty acids or mixtures thereof, a pharmaceutically acceptable alcohol, and water, wherein said solubilized HIV protease inhibiting compounds contained therein have improved solubility properties.

DETAILED DESCRIPTION OF THE INVENTION

The instant invention comprises a solubilized HIV protease inhibiting compound or a combination of solubilized HIV protease inhibiting compounds, or pharmaceutically acceptable salts thereof, in a pharmaceutically acceptable organic solvent comprising a mixture of at least one pharmaceutically acceptable medium and/or long chain fatty acid, a pharmaceutically-acceptable alcohol, and water.

The compositions of the instant invention provide greatly improved solubility for said solubilized HIV protease inhibiting compounds contained therein when compared to analogous compositions without the addition of water.

A preferred composition of the invention is a solution comprising (a) a solubilized HIV protease inhibiting compound or a combination of solubilized HIV protease inhibiting compounds (preferably, a compound of the formula I or II, or saquinavir or nelfinavir or indinavir or, more preferably, ritonavir or ABT-378 or saquinavir or nelfinavir or indinavir, or, most preferably, ritonavir or ABT-378); or a combination of ritonavir or nelfinavir and another HIV protease inhibitor (preferably, ABT-378 or saquinavir or indinavir or nelfinavir, or, more preferably, a combination of ritonavir or nelfinavir and another HIV protease inhibitor (preferably, ABT-378 or saquinavir or indinavir or nelfinavir), or, most preferably, a combination of ritonavir and ABT-378) in the amount of from about 1% to about 50% (preferably, from about 1% to about 40%; more preferably, from about 10% to about 40% by weight of the total solution, (b) a pharmaceutically acceptable organic solvent which comprises (i) a pharmaceutically acceptable medium and/or long chain fatty acid or mixtures thereof in the amount of from about 20% to about 99% (preferably, from about 30% to about 75% by weight of the total solution or (ii) a mixture of (1) a pharmaceutically acceptable medium and/or long chain fatty acid or mixtures thereof in the amount of from about 20% to about 99% (preferably, from about 30% to about 75% by weight of the total solution; (2) ethanol in the amount of from about 1% to about 15% (preferably, from about 3% to about 12%) by weight of the total solution, or, alternatively, propylene glycol in the amount of from about 1% to about 15% (preferably, from about 5% to about 10%); (c) water in the amount of from about 0.4% to about 3.5%; and optionally, (d) a pharmaceutically acceptable surfactant in the amount of from about 0% to about 40% (preferably, from about 2% to about 20% and most preferably, from about 2.5% to about 15%) by weight of the total solution.

In a preferred embodiment of the invention, the solution is encapsulated in a soft elastic gelatin capsule (SEC) or a hard gelatin capsule, or orally ingested after further dilution in an appropriate diluent or vehicle.

Specifically, preferred ratios (w/w) of ritonavir to ABT-378 are from about 1:16 to about 5:1. Even more preferred is a ratio of ritonavir to ABT-378 of from about 1:8 to about 3:1. An even more preferred ratio of ritonavir to ABT-378 is 1:4.

Solutions as described herein may include micellar solutions, which are thermodynamically stable systems formed spontaneously in water above a critical temperature and concentration. Said micellar solutions contain small colloidal aggregates (micelles), the molecules of which are in rapid thermodynamic equilibrium with a measurable concentration of monomers. Micellar solutions exhibit solubilization phenomena and thermodynamic stability.

Preferably, the pharmaceutically acceptable organic solvent comprises from about 50% to about 99% by weight of the total solution. More preferably, the pharmaceutically acceptable organic solvent or mixture of pharmaceutically acceptable organic solvents comprises from about 50% to about 75% by weight of the total solution.

The term "pharmaceutically acceptable medium and/or long chain fatty acid" as used herein refers to saturated or unsaturated $C_8$ to $C_{24}$ fatty acids. Preferred fatty acids are mono-unsaturated $C_{16}$-$C_{20}$ fatty acids which are liquids at room temperature. A most preferred fatty acid is oleic acid, with or without additional medium and/or long chain fatty acids in the mixture. One suitable source of said oleic acid is Henkel Corporation.

The term "pharmaceutically acceptable alcohol" as used herein refers to alcohols which are liquid at room temperature, for example ethanol, propylene glycol, 2-2(ethoxyethoxy)ethanol (Transcutol®, Gattefosse, Westwood, N.J.), benzyl alcohol, glycerol, polyethylene glycol 200, polyethylene glycol 300, polyethylene glycol 400, and the like, or mixtures thereof.

Preferred pharmaceutically acceptable solvents comprise (1) pharmaceutically acceptable medium and/or long chain fatty acid in the amount of from about 40% to about 75% by weight of the total solution; (2) ethanol or propylene glycol in the amount of from about 1% to about 15% by weight of the total solution; and (3) water in the amount of from about 0.4% to about 3.5% by weight of the total solution. More preferred pharmaceutically acceptable solvents comprise (1) a pharmaceutically acceptable medium and/or long chain fatty acid in the amount of from about 40% to about 75% by weight of the total solution and (2) ethanol or propylene glycol in the amount of from about 3% to about 12% by weight of the total solution. Even more preferred pharmaceutically acceptable solvents comprise (1) oleic acid in the amount of from about 40% to about 75% by weight of the total solution and (2) ethanol or propylene glycol in the amount of from about 3% to about 12% by weight of the total solution.

In one embodiment of the invention, a more preferred composition of the invention is a solution comprising (a) solubilized ritonavir in the amount of from about 1% to about 30% (preferably, from about 5% to about 25%) by weight of the total solution, (b) a pharmaceutically acceptable organic solvent which comprises (i) a pharmaceutically acceptable medium and/or long chain fatty acid in the amount of from about 40% to about 99% (preferably, from about 30% to about 75% by weight of the total solution or (ii) a mixture of (1) a pharmaceutically acceptable long chain fatty acid in the amount of from about 40% to about 99% (preferably, from about 30% to about 75% by weight of the total solution and (2) ethanol in the amount of from about 1% to about 15% (preferably, from about 3% to about 12%) by weight of the total solution, (c) water in the amount of from about 0.4% to about 3.5% and (d) a pharmaceutically acceptable surfactant in the amount of from about 0% to about 20% (preferably, from about 2.5% to about 10%) by weight of the total solution.

In a more preferred embodiment of the invention, the solution is encapsulated in a soft elastic gelatin capsule (SEC) or a hard gelatin capsule.

An even more preferred composition of the invention is a solution comprising (a) solubilized ritonavir in the amount of from about 1% to about 30% (preferably, from about 5% to about 25%) by weight of the total solution, (b) a pharmaceutically acceptable organic solvent which comprises (i) oleic acid in the amount of from about 15% to about 99% (preferably, from about 30% to about 75% by weight of the total solution or (ii) a mixture of (1) oleic acid in the amount of from about 15% to about 99% (preferably, from about 30% to about 75% by weight of the total solution and (2) ethanol in the amount of from about 1% to about 15% (preferably, from about 3% to about 12%) by weight of the total solution, (c) water in the amount of from about 0.4% to about 3.5%, and (d) polyoxyl 35 castor oil in the amount of from about 0% to about 20% preferably, from about 2.5% to about 10%) by weight of the total solution.

In an even more preferred embodiment of the invention, the solution is encapsulated in a soft elastic gelatin capsule (SEC) or a hard gelatin capsule.

A most preferred composition of the invention is a solution comprising (a) solubilized ritonavir in the amount of about 10% by weight of the total solution, (b) a pharmaceutically acceptable organic solvent which comprises a mixture of (1) oleic acid in the amount of from about 70% to about 75% by weight of the total solution and (2) ethanol in the amount of from about 3% to about 12%, preferably, about 12%, by weight of the total solution, (c) water in the amount of from about 0.4% to about 1.5% and (d) polyoxyl 35 castor oil in the amount of about 6% by weight of the total solution.

In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of about 0.025% by weight of the total solution.

In one embodiment of the invention, a more preferred composition of the invention is a solution comprising (a) a combination of solubilized HIV protease inhibiting compounds which are ritonavir and ABT-378 in the amount of from about 1% to about 45% (preferably, from about 5% to about 45%) by weight of the total solution, and (b) a pharmaceutically acceptable organic solvent which comprises (i) a pharmaceutically acceptable medium and/or long chain fatty acid in the amount of from about 40% to about 99% (preferably, from about 30% to about 75% by weight of the total solution or (ii) a mixture of (1) a pharmaceutically acceptable long chain fatty acid in the amount of from about 40% to about 99% (preferably, from about 30% to about 75% by weight of the total solution and (2) propylene glycol in the amount of from about 1% to about 15% by weight of the total solution, (c) water in the amount of from about 0.4% to about 3.5% and (d) a pharmaceutically acceptable surfactant in the amount of from about 0% to about 20% (preferably, from about 2.5% to about 10%) by weight of the total solution.

In a more preferred embodiment of the invention, the solution is encapsulated in a soft elastic gelatin capsule (SEC) or a hard gelatin capsule.

An even more preferred composition of the invention is a solution comprising (a) a combination of solubilized HIV protease inhibiting compounds which are ritonavir and ABT-378 in the amount of from about 1% to about 45% (preferably, from about 5% to about 45%) by weight of the total solution, (b) a pharmaceutically acceptable organic solvent which comprises (i) oleic acid in the amount of from about 15% to about 99% (preferably, from about 30% to about 75% by weight of the total solution or (ii) a mixture of (1) oleic acid in the amount of from about 15% to about 99% (preferably, from about 30% to about 75% by weight of the total solution and (2) propylene glycol in the amount of from about 1% to about 8% by weight of the total solution, (c) water in the amount of from about 0.4% to about 3.5%, and (d) polyoxyl 35 castor oil in the amount of from about 0% to about 20% (preferably, from about 2.5% to about 10%) by weight of the total solution.

In an even more preferred embodiment of the invention, the solution is encapsulated in a soft elastic gelatin capsule (SEC) or a hard gelatin capsule.

A most preferred composition of the invention is a solution comprising (a) a combination of solubilized HIV protease inhibiting compounds which are ritonavir and ABT-378 in the amount of about 10% by weight of the total solution, (b) a pharmaceutically acceptable organic solvent which comprises a mixture of (1) oleic acid in the amount of from about 70% to about 75% by weight of the total solution and (2) propylene glycol in the amount of from about 1% to about 15%, preferably, about 6%, by weight of the total solution, (c) water in the amount of from about 0.4% to about 1.5% and (d) polyoxyl 35 castor oil in the amount of about 6% by weight of the total solution.

In a most preferred embodiment of the invention, the solution is encapsulated in a soft elastic gelatin capsule (SEC) or a hard gelatin capsule and the solution also comprises an antioxidant (preferably, BHT (butylated hydroxytoluene)) in the amount of about 0.025% by weight of the total solution.

The amount of water employed in the pharmaceutical composition of the instant invention comprises from about 0.4% to about 3.5% by weight of the total solution of water. Preferably, the weight of the total solution of water is from about 0.4% to about 2.0%; more preferably from about 0.4% to about 1.5%; and the most preferred being about 1%.

In addition, the composition of the invention can comprise antioxidants (for example, ascorbic acid, BHA (butylated hydroxyanisole), BHT (butylated hydroxytoluene), vitamin E, and the like) for chemical stability.

The term "pharmaceutically acceptable acid" as used herein refers to (i) an inorganic acid such as hydrochloric acid, hydrobromic acid, hydroiodic acid and the like, (ii) an organic mono-, di- or tri-carboxylic acid (for example, formic acid, acetic acid, adipic acid, alginic acid, citric acid, ascorbic acid, aspartic acid, benzoic acid, butyric acid, camphoric acid, gluconic acid, glucuronic acid, galactaronic acid, glutamic acid, heptanoic acid, hexanoic acid, fumaric acid, lactic acid, lactobionic acid, malonic acid, maleic acid, nicotinic acid, oxalic acid, pamoic acid, pectinic acid, 3-phenylpropionic acid, picric acid, pivalic acid, propionic acid, succinic acid, tartaric acid, undecanoic acid and the like) or (iii) a sulfonic acid (for example, benzenesulfonic acid, sodium bisulfate, sulfuric acid, camphorsulfonic acid, dodecylsulfonic acid, ethanesulfonic acid, methanesulfonic acid, isethionic acid, naphthalenesulfonic acid, p-toluenesulfonic acid and the like).

The term "pharmaceutically acceptable surfactant" as used herein refers to a pharmaceutically acceptable non-ionic surfactant for example, polyoxyethylene castor oil derivatives (for example, polyoxyethyleneglyceroltriricinoleate or polyoxyl ethylene 35 castor oil (Cremophor® EL, BASF Corp.) or polyoxyethyleneglycerol oxystearate (Cremophor® RH 40 (glycerol polyethyleneglycol oxystearate) or Cremophor® RH 60 (polyethyleneglycol 60 hydrogenated castor oil), BASF Corp., and the like) or block copolymers of ethylene oxide and propylene oxide, also known as polyoxyethylene polyoxypropylene block copolymers or polyoxyethylenepolypropylene glycol, such as Poloxamer®124, Poloxamer® 188, Poloxamer® 237, Poloxamer® 338, Poloxamer® 407, and the like, (BASF Wyandotte Corp.) or a mono fatty acid ester of polyoxyethylene (20) sorbitan (for example, polyoxyethylene (20) sorbitan monooleate (Tween® 80), polyoxyethylene (20) sorbitan monostearate (Tween® 60), polyoxyethylene (20) sorbitan monopalmitate (Tween® 40), polyoxyethylene (20) sorbitan monolaurate (Tweens® 20)) and the like) or a sorbitan fatty acid ester (including sorbitan laurate, sorbitan oleate, sorbitan palmitate, sorbitan stearate and the like). A preferred pharmaceutically acceptable surfactant is polyoxyl 35 castor oil (Cremophor® EL, BASF Corp.), polyoxyethylene (20) sorbitan monolaurate (Tween®) 20), polyoxyethylene (20) sorbitan monooleate (Tween® 80) or a sorbitan fatty acid ester, for example sorbitan oleate. A most preferred pharmaceutically acceptable surfactant is polyoxyl 35 castor oil (Cremophor® EL, BASF Corp.).

As used herein, the term "substantially pure", when used in reference to a polymorph of ritonavir, refers to a polymorph of ritonavir, Form I or Form II, which is greater than about 90% pure. This means that the polymorph of ritonavir does not contain more than about 10% of any other compound and, in particular, does not contain more than about 10% of any other form of ritonavir. More preferably, the term "substantially pure" refers to a polymorph of ritonavir, Form I or Form II, which is greater than about 95% pure. This means that the polymorph of ritonavir does not contain more than about 5% of any other compound and, in particular, does not contain more than about 5% of any other form of ritonavir. Even more preferably, the term "substantially pure" refers to a polymorph of ritonavir, Form I or Form II, which is greater than about 97% pure. This means that the polymorph of ritonavir does not contain more than about 3% of any other compound and, in particular, does not contain more than about 3% of any other form of ritonavir.

As used herein, the term "substantially pure", when used in reference to amorphous ritonavir, refers to amorphous ritonavir which is greater than about 90% pure. This means that the amorphous ritonavir does not contain more than about 10% of any other compound and, in particular, does not contain more than about 10% of any other form of ritonavir. More preferably, the term "substantially pure", when used in reference to amorphous ritonavir, refers to amorphous ritonavir, which is greater than about 95% pure. This means that the amorphous ritonavir does not contain more than about 5% of any other compound and, in particular, does not contain more than about 5% of any other form of ritonavir. Even more preferably, the term "substantially pure", when used in reference to amorphous ritonavir, refers to amorphous ritonavir which is greater than about 97% pure. This means that the amorphous ritonavir does not contain more than about 3% of any other compound and, in particular, does not contain more than about 3% of any other form of ritonavir.

The composition and preparation of soft elastic gelatin capsules is well known in the art. The composition of a soft elastic gelatin capsule typically comprises from about 30% to about 50% by weight of gelatin NF & EP, from about 20% to about 30% by weight of a plasticizer, and from about 25% to about 40% by weight of water. Plasticizers useful in the preparation of soft elastic gelatin capsules are glycerin, sorbitol, or propylene glycol and the like, or combinations thereof. A preferred soft elastic gelatin capsule has a composition comprising gelatin NF & EP (Type 195) (about 42.6% by weight), glycerin (USP) (about 96% active; about 13.2% by weight), purified water (USP) (about 27.4% by weight), sorbitol special (about 16% by weight) and titanium dioxide (USP) (about 0.4% by weight).

The soft elastic gelatin capsule material can also comprise additives such as preservatives, opacifiers, dyes or flavors, and the like.

Various methods can be used for manufacturing and filling the soft elastic gelatin capsules, for example, a seamless capsule method, a rotary method (developed by Scherer) or a method using a Liner® machine or an Accogel® machine, and the like. Also various manufacturing machines can be used for manufacturing the capsules.

Hard gelatin capsules are purchased from Capsugel, Greenwood, S.C. Capsules are filled manually or by capsule filling machine. The target filling volume/weight depends on the potency of the filling solution in combination with the desired dosage strength.

In general, the compositions of this invention can be prepared in the following manner. The pharmaceutically acceptable medium and/or long chain fatty acid and ethanol or propylene glycol and water are mixed at a temperature from 15-30° C., along with the antioxidant. The HIV protease inhibitor, or mixture of HIV protease inhibitors, is added and stirred until dissolved. The pharmaceutically acceptable surfactant is added with mixing. The appropriate volume of the resulting mixture needed to provide the desired dose of the HIV protease inhibiting compound(s) is filled into hard gelatin capsules or soft elastic gelatin capsules.

Similar increases in the solubility of HIV protease inhibitors in oral solution formulations may be obtained by the addition of water in ranges as disclosed herein. Oral solution formulations are disclosed in U.S. Pat. No. 5,484,801, issued Jan. 16, 1996, the disclosure of which is herein incorporated by reference.

EXAMPLES

The following Examples will serve to further illustrate the instant invention.

Powder X-ray diffraction analysis of samples was conducted in the following manner. Samples for X-ray diffraction analysis were prepared by spreading the sample powder (with no prior grinding required) in a thin layer on the sample holder and gently flattening the sample with a microscope slide.

A Nicolet 12/V X-ray Diffraction System was used with the following parameters: X-ray source: Cu-Kα1; Range: 2.00-40.00° Two Theta; Scan Rate: 1.00 degree/minute; Step Size: 0.02 degrees; Wavelength: 1.540562 angstroms.

Characteristic powder X-ray diffraction pattern peak positions are reported for polymorphs in terms of the angular positions (two theta) with an allowable variability of ±0.10°. This allowable variability is specified by the U.S. Pharmacopeia, pages 1843-1844 (1995). The variability of ±0.1° is intended to be used when comparing two powder X-ray diffraction patterns. In practice, if a diffraction pattern peak from one pattern is assigned a range of angular positions (two theta) which is the measured peak position ±0.10° and a diffraction pattern peak from the other pattern is assigned a range of angular positions (two theta) which is the measured peak position ±0.1° and if those ranges of peak positions overlap, then the two peaks are considered to have the same angular position (two theta). For example, if a diffraction pattern peak from one pattern is determined to have a peak position of 5.20°, for comparison purposes the allowable variability allows the peak to be assigned a position in the range of 5.10°-5.30°. If a comparison peak from the other diffraction pattern is determined to have a peak position of 5.35°, for comparison purposes the allowable variability allows the peak to be assigned a position in the range of 5.25°-5.45°. Because there is overlap between the two ranges of peak positions (for example, 5.10°-5.30° and 5.25°-5.45°) the two peaks being compared are considered to have the same angular position (two theta).

Solid state nuclear magnetic resonance analysis of samples was conducted in the following manner. A Bruker AMX-400 MHz instrument was used with the following parameters: CP-MAS (cross-polarized magic angle spinning); spectrometer frequency for 13C was 100.627952576 MHz; pulse sequence was cp2lev; contact time was 2.5 milliseconds; temperature was 27.0° C.; spin rate was 7000 Hz; relaxation delay was 6.000 sec; 1st pulse width was 3.8 microseconds; 2nd pulse width was 8.6 microseconds; acquisition time was 0.034 seconds; sweep width was 30303.0 Hz; 2000 scans.

FT near infrared analysis of samples was conducted in the following manner. Samples were analyzed as neat, undiluted powders contained in a clear glass 1 dram vial. A Nicolet Magna System 750 FT-IR spectrometer with a Nicolet SabIR near infrared fiber optic probe accessory was used with the following parameters: the source was white light; the detector was PbS; the beamsplitter was CaF2; sample spacing was 1.0000; digitizer bits was 20; mirror velocity was 0.3165; the aperture was 50.00; sample gain was 1.0; the high pass filter was 200.0000; the low pass filter was 11000.0000; the number of sample scans was 64; the collection length was 75.9 seconds; the resolution was 8.000; the number of scan points was 8480; the number of FFT points was 8192; the laser frequency was 15798.0 cm$^{-1}$; the interferogram peak position was 4096; the apodization was Happ-Genzel; the number of background scans was 64 and the background gain was 1.0.

FT mid infrared analysis of samples was conducted in the following manner. Samples were analyzed as neat, undiluted powders. A Nicolet Magna System 750 FT-IR spectrometer with a Spectra-Tech InspectIR video microanalysis accessory and a Germanium attenuated total reflectance (Ge ATR) crystal was used with the following parameters: the source was infrared; the detector was MCT/A; the beamsplitter was KBr; sample spacing was 2.0000; digitizer bits was 20; mirror velocity was 1.8988; the aperture was 100.00; sample gain was 1.0; the high pass filter was 200.0000; the low pass filter was 20000.0000; the number of sample scans was 128; the collection length was 79.9 seconds; the resolution was 4.000; the number of scan points was 8480; the number of FFT points was 8192; the laser frequency was 15798.0 cm$^{-1}$; the interferogram peak position was 4096; the apodization was triangular; the number of background scans was 128 and the background gain was 1.0.

Differential scanning calorimetric analysis of samples was conducted in the following manner. A T.A. Instruments Thermal Analyzer 3100 with Differential Scanning Calorimetry module 2910 was used, along with Modulated DSC software version 1.1A. The analysis parameters were: Sample weight: 2.28 mg, placed in a covered, uncrimped aluminum pan; Heating rate: room temperature to 150° C. at 5° C./minute under a nitrogen purge.

Example 1

Preparation of Amorphous Ritonavir

Form I crystalline polymorph of ritonavir (100 g) was melted at 125° C. by heating Form I. The melt was maintained at a temperature of 125° C. for 3 hours. The melt was rapidly cooled by placing the container holding the melt into a Dewar flask containing liquid nitrogen. The resulting glass was ground with a mortar and pestle to provide amorphous ritonavir (100 g). Powder X-ray diffraction analysis confirmed that the product was amorphous. Differential scanning calorimetric analysis determined that the glass transition point was from about 45° C. to about 49° C. (Measured onset at 45.4° C. and which ends at 49.08° C., with a midpoint of 48.99° C.)

Example 2

Preparation of Crystalline Ritonavir (Form II)

Amorphous ritonavir (40.0 g) was dissolved in boiling anhydrous ethanol (100 mL). Upon allowing this solution to cool to room temperature, a saturated solution was obtained. After standing overnight at room temperature, the resulting solid was isolated from the mixture by filtration and was air dried to provide Form II (approximately 24.0 g).

Example 3

Preparation of (2S)-N-((1S)-1-Benzyl-2-((4S,5S)-4-benzyl-2-oxo-1,3-oxazolidin-5-yl)ethyl)-2-((((2-isopropyl-1,3-thiazol-4-yl)methyl)amino)carbonyl)amino)-3-methylbutanamide Example 3a Preparation of (4S,5S)-5-((2S)-2-t-butyloxycarbonylamino-3-phenylpropyl)-4-benzyl-1,3-oxazolidin-2-one (2S,3S,5S)-2-Amino-3-hydroxy-5-t-butyloxycarbonylamino-1,6-diphenylhexane succinate salt (30 g, 63 mmol; U.S. Pat. No. 5,654,466), ((5-thiazolyl)methyl)-(4-nitrophenyl)carbonate hydrochloride (22.2 g; U.S. Pat. No. 5,597,926) and sodium bicarbonate (16.2 g) were mixed with 300 mL of water and 300 mL of ethyl acetate and the mixture was stirred at room temperature for about 30 minutes. The organic layer was then separated and heated at about 60° C. for 12 hours, and then stirred at 20-25° C. for 6 hours. 3 mL of ammonium hydroxide (29% ammonia in water) was added and the mixture stirred for 1.5 hours. The resulting mixture was washed with 4×200 mL of 10% aqueous potassium carbonate and the organic layer was separated and evaporated under vacuum to provide an oil. The oil was suspended in about 250 mL of heptane. The heptane was evaporated under vacuum to provide a yellow solid. The yellow solid was dissolved in 300 mL of THF and 25 mL of 10% aqueous sodium hydroxide was added. After stirring for about 3 hours, the mixture was adjusted to pH 7 by addition of 4N HCl (about 16 mL). The THF was evaporated under vacuum to leave an aqueous residue, to which was added 300 mL of distilled water. After stirring this mixture, a fine suspension of solids resulted. The solid was collected by filtration and the filtered solid was washed with water (1400 mL) in several portions, resulting in the desired product.

Example 3b

Preparation of (4S,5S)-5-((2S)-2-amino-3-phenyl-propyl)-4-benzyl-1,3-oxazolidin-2-one The crude, wet product of Example 3a was slurried in 1N HCl (192 mL) and the slurry was heated to 70° C. with stirring. After 1 hour, THF (100 mL) was added and stirring at 65° C. was continued for 4 hours. The mixture was then allowed to cool to 20-25° C. and was stirred overnight at 20-25° C. The THF was removed by evaporation under vacuum and the resulting aqueous solution was cooled to about 5° C., causing some precipitation to occur. The aqueous mixture was adjusted to pH 7 by addition of 50% aqueous sodium hydroxide (about 18.3 g). The resulting mixture was extracted with ethyl acetate (2×100 mL) at about 15° C. The combined organic extracts were washed with 100 mL of brine and the organic layer was separated and stirred with sodium sulfate (5 g) and Darco G-60 (3 g). This mixture was warmed on a hot plate for 1 hour at 45° C. The hot mixture was then filtered through a bed of diatomaceous earth and the filter pad was washed with ethyl acetate (100 mL). The filtrate was evaporated under vacuum to provide an oil. The oil was redissolved in methylene chloride (300 mL) and the solvent was evaporated under vacuum. The resulting oil was dried at room temperature under vacuum to provide the desired product (18.4 g) as a glassy syrup.

Example 3c

Preparation of (2S)-N-((1S)-1-Benzyl-2-((4S,5S)-4-benzyl-2-oxo-1,3-oxazolidin-5-yl)ethyl)-2-(((( 2-isopropyl-1,3-thiazol-4-yl)methyl)amino)carbonyl)amino)-3-methylbutanamide N-((N-Methyl-N((2-isopropyl-4-thiazolyl)methyl)amino)carbonyl)-L-valine (10.6 g, 33.9 mmol;

U.S. Pat. No. 5,539,122 and International Patent Application No. WO98/00410), the product of Example 3b (10.0 g, 32.2 mmol) and 1-hydroxybenzotriazole (5.2 g, 34 mmol) were dissolved in THF (200 mL). 1,3-dicylclohexylcarbodiimide (DCC, 7.0 g, 34 mmol) was then added to the THF mixture and the mixture was stirred at 22° C. for 4 hours. Citric acid (25 mL of 10% aqueous solution) was added and stirring continued for 30 minutes. The THF was then evaporated under vacuum. The residue was dissolved in ethyl acetate (250 mL) and washed with 10% citric acid solution (175 mL). NaCl (5 g) was added to accelerate the separation of the layers. The organic layer was sequentially washed with 10% aq. sodium carbonate (2×200 mL) and water (200 mL). The organic layer was then dried over sodium sulfate (20 g), filtered and evaporated under vacuum. The resulting product (20.7 g of a foam) was dissolved in hot ethyl acetate (150 mL) and then heptane (75 mL) was added. Upon cooling, another 75 mL of heptane was added and the mixture was heated to reflux. Upon cooling to room temperature, no precipitate formed. The solvents were evaporated under vacuum and the residue was redissolved in a mixture of 200 mL ethyl acetate/ 100 mL heptane. The small amount of undissolved solid was removed by filtration. The filtrate was evaporated under vacuum and the residue was dissolved in a mixture of 100 mL ethyl acetate/50 mL heptane, giving a clear solution. The solution was cooled to −10° C. and a white precipitate formed. The mixture was allowed to sit at −15° C. for 24 hours. The resulting solid was collected by filtration, washed with 1:1 ethyl acetate/heptane (2×24 mL) and dried in a vacuum oven at 55° C. to provide the desired product as a beige solid (16.4 g).

Example 4

Preparation of Crystalline Ritonavir (Form II)

To a solution of 1.595 g of ritonavir Form I in 10 mL of 200 proof ethanol was added approximately 50 micrograms of the product of Example 3c. This mixture was allowed to stand at about 5° C. for 24 hours. The resulting crystals were isolated by filtration through 0.45 micron nylon filter and air dried to provide ritonavir Form II.

Example 5

Alternative Preparation of Crystalline Ritonavir (Form II)

Ethyl acetate (6.0 L/kg of ritonavir) was added to ritonavir (Form I or a mixture of Form I and Form II) in a reaction vessel. The mixture was stirred and heated to 70° C. until all solids were dissolved. The solution was filtered (utilizing a centrifuge pump and 5×20 inch cartridge filters having a porosity of 1.2 microns) and the filtrate was allowed to cool to 52° C. at a rate of 2-10° C./hour. To this solution was added ritonavir Form II seed crystals (about 1.25 g of Form II seed crystals/kg of ritonavir) and the mixture was stirred at 52° C. for not less than 1 hour at an agitation rate of 15 RPM. The mixture was then allowed to cool to 40° C. at a rate of 10° C./hour. Heptane (2.8 L/kg of ritonavir) was added at a rate of 7 L/minute with mixing. The mixture was allowed to cool to 25° C. at a rate of 10° C./hour with mixing. Then the mixture was stirred for not less than 12 hours at 25° C. The product was isolated by filtration using a Heinkel type centrifuge (run time approximately 16 hours). The product was dried at 55° C. under vacuum (50 mm Hg) for 16-25 hours to provide ritonavir crystal Form II.

Example 6

Preparation of Amorphous Ritonavir

Ritonavir Form I (40 g) was dissolved in methylene chloride (60 mL). This solution was slowly added over 15 minutes to a round bottom flask equipped with an overhead stirrer and containing hexanes (3.5 L). The resulting slurry was allowed to stir for 10 minutes. The precipitate was filtered and dried at room temperature in a vacuum oven to provide amorphous ritonavir (40 g).

Example 7

Preparation of Amorphous Ritonavir

Ritonavir Form I (5 g) was dissolved in methanol (8 mL). This solution was slowly added to a round bottom flask equipped with an overhead stirrer and containing distilled water (2 L), while maintaining the internal temperature near 0° C. The resulting solid was filtered to give a sticky solid which was dried in a vacuum oven to give amorphous ritonavir (2.5 g).

Example 8

Comparative Solubilities

Solubility experiments were performed for ritonavir Form I and Form II in various formulation mediums. Data is provided in FIGS. 3-7.

Tables 1 and 2 provided hereinbelow illustrate the pharmaceutical composition without water. Examples 9 and 10 illustrate the pharmaceutical composition with water.

TABLE 1

Composition of Formulations T-1 and T-2.

| Components | T-1 mg/g | T-1 mg/cap | T-2 mg/g | T-2 mg/cap |
|---|---|---|---|---|
| Ritonavir | 200.0 | 200.0 | 200.0 | 200.0 |
| Alcohol, dehydrated, USP | 100.0 | 100.0 | 100.0 | 100.0 |
| Oleic acid, NF | 650.0 | 650.0 | 600.0 | 600.0 |
| Polyoxyl 35 Castor Oil (Cremophor EL ®) | 50.0 | 50.0 | 100.0 | 100.0 |
| BHT | 0.01 | 0.01 | 0.01 | 0.01 |

TABLE 2

Composition of Formulation T-1B.

| Components | T-1 B mg/g | T-1 B mg/cap |
|---|---|---|
| Ritonavir | 200.0 | 200.0 |
| Alcohol, dehydrated, USP | 120.0 | 120.0 |
| Oleic acid, NF | 619.5 | 619.5 |
| Polyoxyl 35 Castor Oil (Cremophor EL ®) | 60.0 | 60.0 |
| BHT | 0.5 | 0.5 |

Example 9

Preparation of Norvir® (100 mg) Soft Gelatin Capsules

The following protocol is employed in the preparation of 1000 soft gelatin capsules:

| Scale (mg/capsule) | Name | Amount (g) |
|---|---|---|
| Q.S. | Nitrogen, N.F. | Q.S. |
| 118.0 | Ethanol, dehydrated, USP, 200 Proof | 118.0 |
| 2.0 | Ethanol, dehydrated, USP, 200 Proof | 2.0 |
| 0.25 | Butylated Hydroxytoluene, NF | 0.25 |
| 704.75 | Oleic Acid, NF | 704.75 |
| 100.0 | Ritonavir | 100.0 |
| 10.0 | Water, purified, USP (distilled) | 10.0 |
| 60.0 | Polyoxyl 35 Castor Oil, NF | 60.0 |
| 5.000 | Oleic Acid, NF | 5.000 |

A mixing tank and suitable container are purged with nitrogen. 118.0 g of ethanol is weighed, blanketed with nitrogen, and held for later use. The second aliquot of ethanol (2 g) is then weighed, and mixed with 0.25 g of butylated hydroxytoluene until clear. The mixture is blanketed with nitrogen and held. The main mixing tank is heated to 28 ° C. (not to exceed 30° C.). 704.75 g of oleic acid is then charged into the mixing tank. 100.0 g of ritonavir is then added to the oleic acid with mixing. The ethanol/butylated hydroxytoluene is then added to the mixing tank, followed by the 118.0 g of ethanol measured previously, and mixed for at least 10 minutes. 10 g of water is then charged into the tank and mixed until the solution is clear (for not less than 30 minutes). The sides of the vessel are scraped for ritonavir, and mixed for not less than an additional 30 minutes. 60.0 g of Polyoxyl 35 castor oil is charged into the tank and mixed until uniform. The solution is stored at 2-8 ° C. until encapsulation. 1.0 g of the solution is filled into each soft gelatin capsule (die: 18 oblong [18BE]; gel: 005L2DDXHB-EP; gel dyes: white 920P). The soft gelatin capsules are then dried, and stored at 2-8 ° C.

Example 10

Preparation of ABT-378/Norvir® (133.3/33.3 mg) Soft Gelatin Capsules

The following protocol is employed in the preparation of 1000 soft gelatin capsules:

| Scale (mg/capsule) | Name | Amount (g) |
|---|---|---|
| Q.S. | Nitrogen, N.F. | Q.S. |
| 578.6 | Oleic Acid, NF | 578.6 |
| 33.3 | Ritonavir | 33.3 |
| 64.1 | Propylene Glycol, USP | 64.1 |
| 4.3 | Water, purified, USP (distilled) | 4.3 |
| 133.3 | ABT-378 | 133.3 |
| 10.0 | Oleic Acid, NF | 10.0 |
| 21.4 | Polyoxyl 35 Castor Oil, NF | 21.4 |
| 10.0 | Oleic Acid, NF | 10.0 |

A mixing tank and suitable container are purged with nitrogen. 578.6 g of oleic acid is then charged into the mixing tank. The mixing tank is heated to 28° C. (not to exceed 31° C.) and mixing is started. 33.3 g of ritonavir is then added to the oleic acid with mixing. The propylene glycol and water are added to the mixing tank, and mixing is continued until the solution is clear. 133.3 g of ABT-378 is then added into the mixing tank, and mixing is continued. 10 g of oleic acid is then charged into the tank and mixed until the solution is clear. 21.4 g of polyoxy 35 Castor Oil, NF is added to the mixing tank, and mixing is continued, followed by the addition of 10 g of Oleic Acid. NF. A sample is collected, and the solution is stored at 2-8° C. until encapsulation. 0.855 (+/1 3%) g of the solution is filled into each soft gelatin capsule (die: 12BF; gel: L1.25DDXHBHM-EP; gel dye: Orange 419T-EP). The soft gelatin capsules are then inspected and cleaned, and stored at 2-8° C.

Example 11

Protocol for Oral Bioavailability

Dogs (beagle dogs, mixed sexes, weighing 7-14 kg) were fasted overnight prior to dosing, but were permitted water ad libitum. Each dog received a 100 µg/kg subcutaneous dose of histamine approximately 30 minutes prior to dosing. Each dog received a single dosage form corresponding to a 5 mg/kg dose of the drug. The dose was followed by approximately 10 milliliters of water. Blood samples were obtained from each animal prior to dosing and 0.25, 0.5, 1.0, 1.5, 2, 3, 4, 6, 8, 10, and 12 hours after drug administration. The plasma was separated from the red cells by centrifugation and frozen (−30° C.) until analysis. Concentrations of parent drug were determined by reverse phase HPLC with low wavelength UV detection following liquid-liquid extraction of the plasma samples. The parent drug area under the curve was calculated by the trapezoidal method over the time course of the study. The absolute bioavailability of each test composition was calculated by comparing the area under the curve after oral dosing to that obtained from a single intravenous dose. Each capsule or capsule composition was evaluated in a group containing at least six dogs; the values reported are averages for each group of dogs.

We claim:

1. A pharmaceutical composition comprising a solution which comprises:
   (a) (2S,3S,5S)-5-(N-(N-((N-methyl-N-((2-isopropyl-4-thiazolyl)-methyl)amino)carbonyl)-L-valinyl)amino)-2-(N-((5-thiazolyl)methoxy-carbonyl)-amino-1,6-diphenyl-3-hydroxyhexane (ritonavir), or a combination of ritonavir and another HIV protease inhibiting compound;
   (b) a pharmaceutically acceptable medium and/or long chain fatty acid in an amount of from 30% to 75% by weight of said solution;
   (c) water in an amount of from 0.4% to 3.5% by weight of said solution; and, optionally,
   (d) a pharmaceutically acceptable surfactant.

2. The composition according to claim 1, wherein said solution comprises ritonavir and said another HIV protease inhibiting compound.

3. The composition according to claim 2, wherein said another HIV protease inhibiting compound is (2S,3S,5S)-2-(2,6-dimethylphenoxyacetyl)-amino-3-hydroxy-5-(2S-(1-tetrahydropyrimid-2-onyl)-3-methyl-butanoyl)amino-1,6-diphenylhexane (ABT-378).

4. The composition according to claim 2, wherein said another HIV protease inhibiting compound is a compound selected from the group consisting of:
   (1) (2S,3S,5S)-2-(2,6-dimethylphenoxyacetyl)-amino-3-hydroxy-5-(2S-(1-tetrahydropyrimid-2-onyl)-3-methyl-butanoyl)amino-1,6-diphenylhexane,
   (2) N-(2(R)-hydroxy-1(S)-indanyl)-2(R)-phenylmethyl-4(S)-hydroxy-5-( 1-(4-(3-pyridylmethyl)-2(S)-N'-(t-butylcarboxamido)-piperazinyl))-pentaneamide (indinavir),
   (3) N-tert-butyl-decahydro-2-[2(R)-hydroxy-4-phenyl-3(S)-[[N-(2-quinolylcarbonyl)-L-asparaginyl]amino]butyl]-(4aS ,8aS)-isoquinoline-3 (S)-carboxamide (saquinavir),
   (4) 5(S)-Boc-amino-4(S)-hydroxy-6-phenyl-2(R)-phenylmethylhexanoyl-(L)-Val-(L)-Phe- morpholin-4-ylamide,
   (5) 1-Naphthoxyacetyl-beta-methylthio-Ala-(2S,3 S)-3-amino-2-hydroxy-4-butanoyl 1,3-thiazolidine-4-t-butylamide,
   (6) 5-isoquinolinoxyacetyl-beta-methylthio-Ala-(2S ,3S)-3-amino-2-hydroxy-4-butanoyl-1,3- thiazolidine-4-t-butylamide,
   (7) [1S-[1R-(R-),2S *])-N¹[3-[[[(1,1-dimethylethyl)amino]carbonyl](2-methylpropyl)amino]-2-hydroxy-1-(phenylmethyl)propyl]-2-[(2-quinolinylcarbonyl)amino]-butanediamide,
   (8)

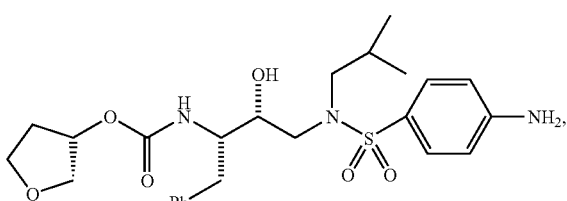

(9)

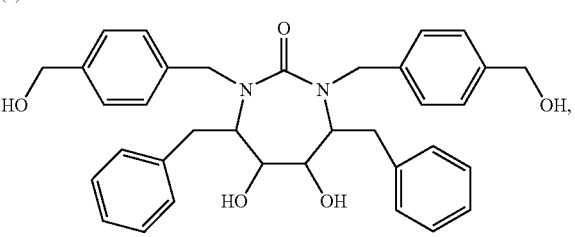

(10)

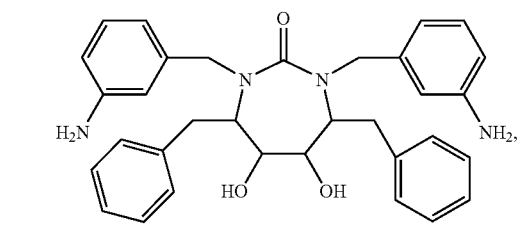

(11)

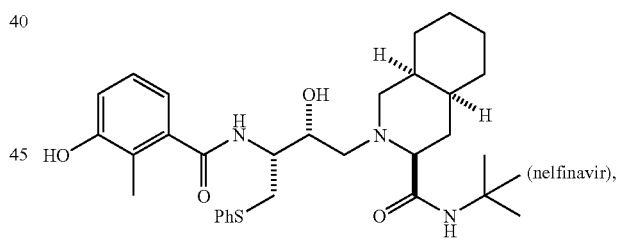

(nelfinavir), (12)

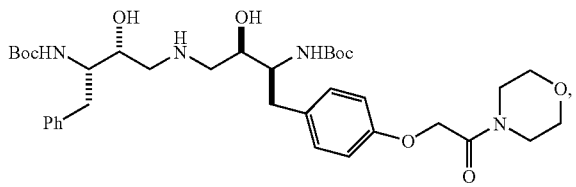

(13)

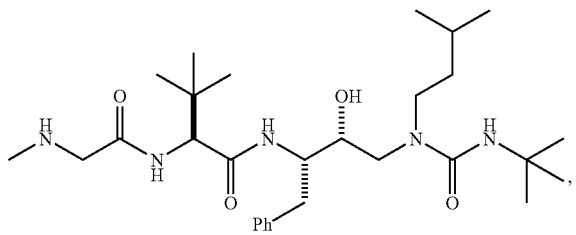

-continued (14)

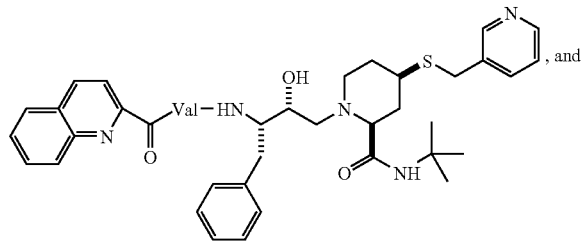

, and (15)

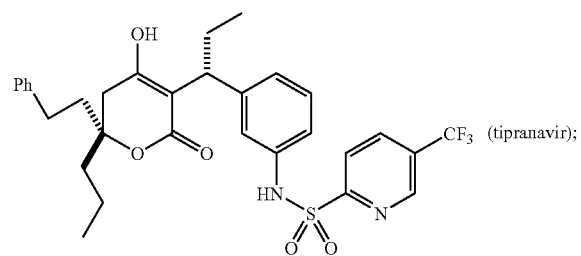

(tipranavir);

or a pharmaceutically acceptable salt thereof.

5. The composition according to claim 1, wherein said pharmaceutically acceptable surfactant which is in an amount of from 2% to 20% by weight of said solution.

6. The composition according to claim 1, wherein said solution comprises ritonavir, or a combination of ritonavir and said another HIV protease inhibiting compound, in an amount of from 10 to 40% by weight of said solution.

7. The composition of claim 1, wherein said solution comprises water in an amount of from 0.4% to 1.5% by weight of said solution.

8. The composition according to claim 1, wherein said pharmaceutically acceptable medium and/or long chain fatty acid is a mono-unsaturated $C_{16}$-$C_{20}$ fatty acid which is liquid at room temperature.

9. The composition according to claim 1, wherein said pharmaceutically acceptable medium and/or long chain fatty acid is oleic acid.

10. The composition according to claim 1, wherein comprises oleic acid in an amount of from 30% to 75% by weight of said solution.

11. The composition according to claim 1, wherein said solution comprises polyoxyl 35 castor oil.

12. The composition according to claim 1, wherein said solution comprises:
(a) ritonavir in an amount from 1% to 30% by weight of said solution;
(b) a pharmaceutically acceptable medium and/or long chain fatty acid in an amount of from 30% to 75% by weight of said solution;
(c) water in an amount of from 0.4% to 3.5% by weight of said solution; and
(d) a pharmaceutically acceptable surfactant in an amount of from 0% to 20% by weight of said solution.

13. The composition of claim 1, wherein said solution comprises:
(a) a combination of ritonavir and (2S,3S,5S)-2-(2,6-dimethylphenoxyacetyl)amino-3-hydroxy-5-[2S-(1-tetrahydropyrimid-2-onyl)-3-methylbutanoyl]-amino-1,6-diphenylhexane, in an amount of from 1% to 45% by weight of said solution;
(b) a pharmaceutically acceptable medium and/or long chain fatty acid in an amount of from 30% to 75% by weight of said solution;
(d) water in an amount of from 0.4% to 3.5% by weight of said solution; and
(e) a pharmaceutically acceptable surfactant in an amount of from 0% to 20% by weight of said solution.

14. The composition according to claim 1, wherein said solution comprises:
(a) ritonavir in an amount from 1% to 30% by weight of said solution;
(b) oleic acid in an amount of from 30% to 75% by weight of said solution;
(c) water in an amount of from 0.4% to 3.5% by weight of said solution; and
(d) polyoxyl 35 castor oil in an amount of from 0% to 20% by weight of said solution.

15. The composition of claim 14, wherein said solution comprises polyoxyl 35 castor oil in an amount of from 2.5% to 10% by weight of said solution.

16. The composition of claim 1, wherein said solution comprises:
(a) a combination of ritonavir and (2S,3S,5S)-2-(2,6-dimethylphenoxyacetyl)amino-3-hydroxy-5-[2S-(1-tetrahydropyrimid-2-onyl)-3-methylbutanoyl]-amino-1,6-diphenylhexane, in an amount of from 1% to 45% by weight of said solution;
(b) oleic acid in an amount of from 30% to 75% by weight of said solution;
(c) water in an amount of from 0.4% to 3.5% by weight of said solution; and
(d) polyoxyl 35 castor oil in an amount of from 0% to 20% by weight of said solution.

17. The composition of claim 16, wherein said solution comprises polyoxyl 35 castor oil in an amount of from 2.5% to 10% by weight of said solution.

18. The composition according to claim 1, further comprising a hard or soft elastic gelatin capsule which encapsulates said solution.

19. The composition according to claim 2, further comprising a hard or soft elastic gelatin capsule which encapsulates said solution.

20. The composition according to claim 3, further comprising a hard or soft elastic gelatin capsule which encapsulates said solution.

21. The composition according to claim 10, further comprising a hard or soft elastic gelatin capsule which encapsulates said solution.

22. The composition according to claim 12, further comprising a hard or soft elastic gelatin capsule which encapsulates said solution.

23. A pharmaceutical composition comprising a solution which comprises:
(a) ritonavir, or a combination of ritonavir and another HIV protease inhibiting compound;
(b) a mixture of pharmaceutically acceptable medium and/or long chain fatty acids in an amount of from 30% to 75% by weight of said solution;
(c) water in an amount of from 0.4% to 3.5% by weight of said solution; and, optionally,
(d) a pharmaceutically acceptable surfactant.

24. The composition according to claim 23, wherein said mixture of pharmaceutically acceptable medium and/or long chain fatty acids is a mixture of mono-unsaturated $C_{16}$-$C_{20}$ fatty acids which are liquids at room temperature.

25. The composition according to claim 23, wherein said mixture of pharmaceutically acceptable medium and/or long chain fatty acids includes oleic acid.

* * * * *